US011813245B2

(12) United States Patent
Elliott et al.

(10) Patent No.: US 11,813,245 B2
(45) Date of Patent: *Nov. 14, 2023

(54) SULCARDINE ADMINISTRATION FOR TREATMENT OF ACUTE ATRIAL FIBRILLATION

(71) Applicant: HUYABIO International, LLC, San Diego, CA (US)

(72) Inventors: Gary Elliott, San Diego, CA (US); Mireille Gillings, San Diego, CA (US); Robert Goodenow, San Diego, CA (US); Jay Mason, San Diego, CA (US); Waldemar Radziszewski, San Diego, CA (US); Suzanne Romano, San Diego, CA (US)

(73) Assignee: HUYABIO International, LLC, San Diego, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 17/345,564

(22) Filed: Jun. 11, 2021

(65) Prior Publication Data

US 2021/0386708 A1 Dec. 16, 2021

Related U.S. Application Data

(60) Provisional application No. 63/038,664, filed on Jun. 12, 2020.

(51) Int. Cl.
*A61K 31/4025* (2006.01)
*A61K 9/00* (2006.01)
*A61P 9/06* (2006.01)
*A61K 45/06* (2006.01)

(52) U.S. Cl.
CPC ........ *A61K 31/4025* (2013.01); *A61K 9/0053* (2013.01); *A61K 45/06* (2013.01); *A61P 9/06* (2018.01)

(58) Field of Classification Search
CPC .................................................. A61K 31/4025
See application file for complete search history.

(56) References Cited

U.S. PATENT DOCUMENTS

| 6,605,635 | B1 * | 8/2003 | Bai ........................... A61P 9/06 548/518 |
| 8,541,464 | B2 * | 9/2013 | Elliott ................ A61K 31/4025 514/422 |
| 8,637,566 | B2 * | 1/2014 | Elliott ....................... A61P 9/06 514/422 |
| 10,143,626 | B2 | 12/2018 | Li |
| 10,258,575 | B2 | 4/2019 | Li |
| 10,363,220 | B2 | 7/2019 | Li |
| 11,020,374 | B2 * | 6/2021 | Romano ............. C07D 403/10 |
| 11,364,223 | B2 * | 6/2022 | Romano .................. A61P 9/06 |
| 2012/0245214 | A1 | 9/2012 | Elliott |
| 2012/0309810 | A1 | 12/2012 | Elliott |
| 2019/0192440 | A1 | 6/2019 | Li |
| 2020/0316024 | A1 | 10/2020 | Romano et al. |
| 2021/0038568 | A1 | 2/2021 | Romano et al. |

FOREIGN PATENT DOCUMENTS

| CN | 1939298 A | 4/2007 |
| WO | WO-2018/137686 A1 | 8/2018 |
| WO | WO-2020/123824 A1 | 6/2020 |

OTHER PUBLICATIONS

A Phase 1, randomised, double-blind, placebo-controlled, serial cohort doseescalation study of intravenously administered HBI-3000. Clinicaltrials.gov study# NCT03397641 (2018).
"Abstracts from the 2009 Annual Meeting of the International Society for Heart Research North American Section: New Discoveries for Prevention and Treatment of Heart Disease," Baltimore, MD, United States. May 26, 2009-May 29, 2009. Journal of Molecular and Cellular Cardiology 46(5, Supp. 1) (2009).
"Huya completes pre-IND consultation meeting with the FDA for sulcardine sulfate; sulcardine sulfate (430340)," Jun. 19, 2008, retrieved from the internet: http://integrity.thomsonpharma.com/integrity/xmlxsl/pk_ref_list.xml_show_ficha_ref?p_ref_id=1222927.
Bai et al., "Discovery of N-(3,5-bis(1-pyrrolidylmethyl)-4-hydroxybenzyl)-4-methoxybenzenesulfamide (sulcardine) as a novel anti-arrhythmic agent," ACTA Pharmacologica Sinica 33(9):1176-1186 (2012).
Chen et al., "Characteristics of hERG and hNav1 .5 channel blockade by sulcardine sulfate, a novel anti-arrhythmic compound," European Journal of Pharmacology 844, 2019, pp. 130-138.
Chen, Qian, et al. "Pharmacokinetics, safety, and tolerability of sulcardine sulfate: an open-label, single-dose, randomized study in healthy Chinese subjects." *Fundamental & clinical pharmacology* 31.1 (2017): 120-125.
"Guidance of Industry—Estimating the Maximum Safe Starting Dose in Initial Clinical Trials for Therapeutics in Adult Healthy Volunteers," U.S. Department of Health and Human Services, Pharmacology and Toxicology, Jul. 2005, 30 pages.
Guo et al., "Electrophysiologic Properties of HBI-3000: A New Antiarrhythmic Agent with Multiple-channel Blocking Properties in Human Ventricular Myocytes," Journal of Cardiovascular Pharmacology, vol. 57, No. 1, Jan. 2011, pp. 79-85.
Jia et al., "Determination of the novel antiarrhythmic drug sulcardine sulfate in human plasma by liquid chromatography tandem mass spectrometry and its application in a clinical pharmacokinetic study," Biomedical Chromatography 30(8), 2016, pp. 1291-1296.
Lapointe, et al., "Continuous intravenous quinidine infusion for the treatment of atrial fibrillation or flutter: A case series." American Heart Journal 139.1, Jan. 2000, pp. 114-121.
Lee at al., "HBI-3000 Prevents Secondary Sudden Cardiac Death," Journal of Cardiovascular Pharmacology and Therapeutics 18(5), 2013, pp. 453-459.
Lee et al., HBI-3000 Prevents Sudden Cardiac Death in a Conscious Canine Model., Cardiac Electro physiology Society, CES Annual Meeting. Chicago, IL, United States. Nov. 13, 2010-Nov. 13, 2010; Heart Rhythm 7(11), p. 1712.

(Continued)

*Primary Examiner* — Rei Tsang Shiao
(74) *Attorney, Agent, or Firm* — Eversheds Sutherland (US) LLP

(57) ABSTRACT

Provided herein are compositions and methods for administration of sulcardine to a subject in need thereof.

45 Claims, No Drawings

(56) References Cited

OTHER PUBLICATIONS

Lee, et al., "Antifibrillatory actions of HBI-3000 in the conscious canine model of sudden cardiac death," *The FASEB Journal*, vol. 23, Issue 51, Apr. 1, 2009, pp. LB376-LB376.
Lu et al., "Oral Bioavailability and Mass Balance Studies of a Novel Anti-arrhythmic Agent Sulcardine Sulfate in Sprague-Dawley Rats and Beagle Dogs," European Journal of Drug Metabolism and Pharmacokinetics 42(3), 2017, pp. 453-459.
"Drugs in Japan," Medicinal Drug Collection, Jiho Takeda, 27th Edition, 2004, p. 2631, p. 2386.
PCT/US2019/066003 International Search Report and Written Opinion dated Mar. 20, 2020 (9 Pages).
PCT/US2020/015370 International Search Report and Written Opinion dated Jun. 6, 2020 (17 Pages).
PCT/US2020/015370 Invitation to Pay Additional Fees dated May 15, 2020 914 Pages).
Qi, et al., "Innovative drug R&D in China," Nature Reviews Drug Discovery, vol. 10, No. 5, May 2011, pp. 333-334.
Singh, et al., "N-Acylated sulfonamide sodium salt: A prodrug of choice for the bifunctional 2-hydroxymethyl-4-(5-phenyl-3-trifluoromethyl-pyrazol-1-yl) benzenesulfonamide class of COX-2 inhibitors," Bioorganic & Medicinal Chemistry Letters, vol. 16, May 11, 2006, pp. 3921-3926.
Streitwiesser et al., "Introduction to Organic Chemistry", Macmillan Publishing Co., 1992, p. 736.
Wang et al., "Multiple Dose Pharmacokinetics and Safety of Sulcardine Sulfate in Healthy Chinese Male Subjects: An Open-Label Phase I Clinical Study," European Journal of Drug Metabolism and Pharmacokinetics 42(4), 2017, pp. 593-599.
Wang, et al., "Effect of Sulcardine on cardiac electrophysiology in anesthetized rabbits," Chinese Pharmacological Society Communication vol. 19, No. 4, Nov. 4, 2002, pp. 63-64.
Wang, et al., "Electrophysiological Characterization of a Novel Artiarrhythmic Agent—Sulcardine Salts," AACTA Pharmacologica Sinica, Jul. 2006. vol. 27, Suppl. 1, p. 123.

* cited by examiner

SULCARDINE ADMINISTRATION FOR TREATMENT OF ACUTE ATRIAL FIBRILLATION

CROSS-REFERENCE

This application claims the benefit of U.S. Application No. 63/038,664, filed Jun. 12, 2020, which is hereby incorporated by reference in its entirety.

FIELD

The present teachings relate to compositions and methods for administration of sulcardine to a subject in need thereof.

BACKGROUND

U.S. Pat. Nos. 8,541,464 and 8,637,566 (each of which is incorporated herein by reference in its entirety) describe the activity of N-[4-hydroxy-3,5-bis(1-pyrrolidinylmethyl)benzyl]-4-methoxybenzenesulfonamide (hereinafter "sulcardine") and its pharmaceutically acceptable salts, in addition to various uses and methods of administering sulcardine in therapeutically effective amounts to subjects in need thereof.

Chen et al. reports the pharmacokinetics profiles of sulcardine in humans when administered orally. See Chen et al., "Pharmacokinetics, safety, and tolerability of sulcardine sulfate: an open-label, single-dose, randomized study in healthy Chinese subjects", *Fundamental & Clinical Pharmacology.* 31 (2017) 120-125.

There remains a need for developing formulations and methodology for alternative administration of sulcardine in humans to achieve different but desirable pharmacokinetic and efficacy profiles.

SUMMARY

In one embodiment, provided herein are compositions for administering sulcardine in therapeutically effective amounts for the treatment of atrial fibrillation or atrial flutter. In one embodiment, provided herein are compositions for enhanced and safer administration of sulcardine in therapeutically effective amounts.

In one aspect, presented herein is a pharmaceutical composition comprising sulcardine or a pharmaceutically acceptable salt thereof, wherein the composition produces ECG parameter changes in QRS, PDur, PR, or OTcF, or any combination thereof, of no more than about 25%. In some embodiments, the pharmaceutical composition is an inhibitor of $Na_L$, INa; and LCa; characterized by ECG parameter changes in:: (i) a reduction or no change in JTpc of NMT of about 15-25 msec; and (ii) no effect or increase in TpTe. In some embodiments, the pharmaceutical composition results in inhibition of early after depoloarizations (EADs). In some embodiments, the ECG parameters further comprise heart rate. In some embodiments, pharmaceutical composition produces a bimodal effect on QTc including prolongation in QTc at lower drug exposure levels (doses) in association with predominantly INa cardiac ion channel inhibition followed by a potential plateauing or decrease in QTc interval at higher drug exposure levels (doses) associated with increasing inhibitory effect on $Na_L$ and ICa cardiac ion channels.. In some embodiments, the ECG changes occur prior to, in proximity to or at about Tmax with magnitude of changes reflecting plasma concentrations following Tmax in association with drug distribution into periphery. In some embodiments, the pharmaceutical composition has no material (clinically meaningful) effect on heart rate or increase or decreases diastolic and/or systolic blood pressure by no more than about 25% prior to, or at Tmax. In some embodiments, the pharmaceutical composition does not induce $2^{nd}$ or $3^{rd}$ degree heart block.

In some embodiments, the pharmaceutically acceptable salt is ethane-1,2-disulfonic acid, naphthalene-1,5-disulfonic acid, 1-hydroxy-2-naphthoic acid, naphthalene-2-sulfonic acid, dihydro sulfonic acid, hydrochloric acid, or hydrobromic acid. In some embodiments, the composition comprises 200 mg, 350 mg, 500 mg, or 600 mg of sulcardine, or a pharmaceutically acceptable salt thereof. In some embodiments, the mg dosages are calculated form the free base of sulcardine. In some embodiments, the composition is administered to a subject in need thereof. In some embodiments the administration is parenteral administration or oral consumption.

In some embodiments, a pharmaceutical composition is provided comprising sulcardine or a pharmaceutically acceptable salt thereof, wherein the composition produces a mean average plasma profile characterized by a Cmax for the composition in a subject, after administering 200 mg of the compound, of at least about 1,500 ng/mL at about the Tmax, and at most 25% of Cmax at about 1.0 hours after administration.

In some embodiments, a pharmaceutical composition is provided comprising sulcardine or a pharmaceutically acceptable salt thereof, wherein the composition produces a mean average plasma profile characterized by a Cmax for the compound in a subject, after administering 350 mg of the compound, of at least about 3,000 ng/mL at about the Tmax, and at most 25% of Cmax at about 1.0 hours after administration.

In some embodiment, a pharmaceutical composition is provided comprising sulcardine or a pharmaceutically acceptable salt thereof, wherein the composition produces a mean average plasma profile characterized by a Cmax for the compound in a subject, after administering 500 mg of the compound, of at least about 4,000 ng/mL at about Tmax, and at most 25% of Cmax at about 1.0 hours after administration.

In some embodiment, a pharmaceutical composition is provided comprising sulcardine or a pharmaceutically acceptable salt thereof, wherein the composition produces a mean average plasma profile characterized by a Cmax for the compound in a subject, after administering 600 mg of the compound, of at least about 5,500 ng/mL at about Tmax, and at most 25% of Cmax at about 1.0 hours after administration.

In another embodiment, provided herein is a method of treating atrial fibrillation (AF) or atrial flutter, comprising administering to a human subject in need thereof sulcardine, or a pharmaceutically acceptable salt thereof, resulting in robust, albeit temporary, increase of QRS, PDur, PR, changes in QTc attendant with a reduction or no change in JTpc and no effect or increase in TpTe. In one embodiment, without being limited by a particular theory, these changes in ECG parameters are associated with rapid accumulation of the drug in the bloodstream through intravenous infusion or other parenteral routes of administration combined with rapid inherent redistribution of the drug from the bloodstream and highly vascularized organs such as the heart to secondary compartments. Such a profile leads to rapid and significant changes in relevant ECG parameters associated with temporally linked cardioversion from atrial fibrillation to sinus rhythm followed by rapid reversal of ECG parameter changes upon drug redistribution, lessening risk of proarrhythmic events associated with QT, PR and QRS prolongation.

In another embodiment, provided herein is a method of treating atrial fibrillation (AF) or atrial flutter, comprising administering to a human subject in need thereof, sulcardine or a pharmaceutically acceptable salt thereof, resulting in: (i) an increases of less than about 25% in QRS, PDur, PR, and QTcF; (ii) a reduction of less than 25 msec or no change in JTpc; and/or (iii) no effect or increase in TpTe. In some embodiments, the composition produces a change in QTcF interval that does not increase by more than about 20% after administering of the pharmaceutical composition. In some embodiments, the composition produces an increased in QTcF interval from about 5% to about 20% after the administration. In some embodiments, the plasma concentration is decreases by at least about 75% within about 1 hour after administration.

In another aspect, provided herein is a method of treating atrial fibrillation (AF) or atrial flutter, comprising administering to a human subject in need thereof sulcardine, or a pharmaceutically acceptable salt thereof, wherein an amount of sulcardine, or a pharmaceutically acceptable salt thereof is sufficient to achieve a Tmax of plasma concentration of sulcardine, or a pharmaceutically acceptable salt thereof of about less than 2.0 hours.

In some embodiments, sulcardine or a pharmaceutically acceptable salt thereof, is administered over a period of less than about 1 hour. In some embodiments, sulcardine or a pharmaceutically acceptable salt thereof, is administered over a period of about 30 minutes. In some embodiments, sulcardine or a pharmaceutically acceptable salt thereof, is administered at a rate that does not produce an arrhythmia or a clinically significant change in heart rate or blood pressure.

In some embodiments, the AF is acute AF. In some embodiments, the AF is paroxysmal AF. In some embodiments, the AF is recurring AF. In some embodiments, the treatment is for atrial flutter.

These and other features, aspects and advantages of the present teachings will become better understood with reference to the following description, examples and appended claims.

DETAILED DESCRIPTION

Definitions

Unless indicated otherwise, the terms and phrases used in this description have the following meanings:

As used herein and unless otherwise specified, sulcardine (free base form) has a chemical name of N-[4-hydroxy-3,5-bis(1-pyrrolidinylmethyl)benzyl]-4-methoxybenzenesulfonamide, and has the following structure:

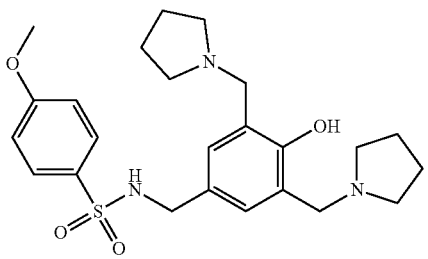

In some embodiments, the pharmaceutically acceptable salt is ethane-1,2-disulfonic acid, naphthalene-1,5-disulfonic acid, 1-hydroxy-2-naphthoic acid, naphthalene-2-sulfonic acid, dihydro sulfonic acid, hydrochloric acid, or hydrobromic acid. In some embodiments, the pharmaceutically acceptable salt is ethane-1,2-disulfonic acid. In some embodiments, the pharmaceutically acceptable salt is naphthalene-1,5-disulfonic acid. In some embodiments, the pharmaceutically acceptable salt is 1-hydroxy-2-naphthoic acid. In some embodiments, the pharmaceutically acceptable salt is naphthalene-2-sulfonic acid. In some embodiments, the pharmaceutically acceptable salt is hydrochloric acid or hydrobromic acid.

In some embodiments, the pharmaceutically acceptable salt is sulcardine sulfate.

As used herein and unless otherwise specified, sulcardine sulfate has the following structure:

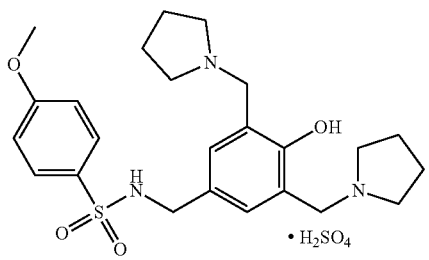

In one embodiment, the sulcardine sulfate is sulcardine sulfate trihydrate.

As used herein and unless otherwise specified, "Cmax" refers to maximum plasma concentration.

As used herein and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

"Treat," "treatment," and "treating" are employed in this description to refer to administering a pharmaceutical composition or formulation for prophylactic and/or therapeutic purposes. The term "therapeutic treatment" refers to administering treatment to a patient already suffering from a condition such as arrhythmia. Thus, in preferred embodiments, treating is the administration to a mammal of therapeutically effective amounts of an anti-arrhythmic agent.

A "subject" of treatment is a prokaryotic or a eukaryotic cell, a tissue culture, a tissue or an animal, e.g., a mammal, including a human. Non-human animals subject to treatment include, for example, a simian, a murine, a canine, a leporid, such as a rabbit, livestock, sport animals, and pets. As used herein and unless otherwise specified, a "patient" is a human subject.

A "treatment population" refers to a group of clinically typical patients receiving the treatment and a typical response that would be expected from said patents.

An "anti-arrhythmic agent," as used herein, refers to a molecule having a therapeutic effect of treating arrhythmia or alleviating associated symptoms in a subject. Non-limiting examples of arrhythmias include supraventricular tachyarrhythmia such as atrial fibrillation, premature ventricular contractions, ventricular tachycardia, and ventricular fibrillation. In one aspect, an anti-arrhythmic agent is sulcardine, or a pharmaceutically acceptable salt thereof. In another aspect, an anti-arrhythmic agent is sulcardine sulfate.

As used herein, a pharmaceutically acceptable salt of sulcardine can be the active agent in a formulation useful for treating arrhythmia. Illustrative of such sulcardine salts are: (A) inorganic acid salts such as acetate, borate, bicarbonate, sulfate, hydrochloride, bromides, chlorides, iodide, hydrobromide, hydroiodide, nitrate, phosphate, diphosphate, and fluorophosphate salts; (B) organic acid salts such as amsonate (4,4-diaminostilbene-2,2-disulfonate), bitartrate, butyrate, citrate, calcium edetate, camsylate, edisylate, estolate, esylate, glutamate, gluconate, gluceptate, lactate, lactobionate, laurate, malate, maleate, mandelate, methylbromide, methylnitrate, methylsulfate, mucate, oleate, oxalate, palmitate, pamoate (1,1-methene-bis-2-hydroxy-3-naphthoate, einbonate), pamoate, pantothenate, salicylate, stearate, subacetate, succinate, sulfate, sulfosalicylate, suramate, propionate, valerate, fiunarate, fumarate, and tartrate salts; and (C) alkali metal salts and alkali earth salts, such as the sodium, potassium, lithium and calcium salts of sulcardine. In this context, a pharmaceutically acceptable salt can have more than one charged atom in its structure and, hence, one or more counterions.

The phrases "effective amount," "therapeutically effective amount," and "pharmaceutically effective amount" denote an amount of an active agent, such as an anti-arrhythmic agent as presently disclosed, that has a therapeutic effect. The doses of the active agent which are useful in treatment are therapeutically effective amounts. Thus, a therapeutically effective amount is an amount of the active agent that produces the desired therapeutic effect, as judged by clinical trial results and/or model animal studies. In particular embodiments, the active agent is administered in a pre-determined dose; hence, a therapeutically effective amount would be an amount of the dose administered. This amount also can depend upon the patient's height, weight, sex, age and medical history.

A "carrier" or "excipient" is a compound or material used to facilitate administration of the compound, for example, to control the release and/or bioavailability of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); GOODMAN AND GILMAN'S: THE PHARMACOLOGICAL BASIS OF THERAPEUTICS, 8th Ed., Pergamon Press.

The phrases "pharmaceutically acceptable carrier" and "pharmaceutically acceptable excipient" can note any and all solvents, dispersion media, coatings, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. Suitable pharmaceutically acceptable excipients include, but are not limited to, buffers, diluents, tonicity agents, stabilizers, antioxidants, preservatives and mixtures thereof.

The term "buffer" denotes a pharmaceutically acceptable excipient, which stabilizes the pH of a pharmaceutical preparation. Suitable buffers are known in the art and can be found in the literature. Pharmaceutically acceptable buffers comprise but are not limited to glycine-buffers, histidine-buffers, citrate-buffers, succinate-buffers and phosphate-buffers. Independently from the buffer used, the pH can be adjusted at a value from about 2 to about 9, or alternatively from about 2.5 to about 7, or alternatively from about 3 to about 5 or alternatively about 3 with an acid or a base known in the art, e.g., succinic acid, hydrochloric acid, acetic acid, phosphoric acid, sulfuric acid and citric acid, sodium hydroxide and potassium hydroxide.

Suitable buffers include, without limitation, glycine buffer, histidine buffer, 2-morpholinoethanesulfonic acid (MES), cacodylate, phosphate, acetate, succinate, and citrate. In one aspect, the buffer is a glycine buffer. In another aspect, the buffer is a histine buffer. The concentration of the buffer can be between about 1 mM and about 100 mM, or alternatively about 2 mM to about 40 mM, or alternatively about 5 mM to about 20 mM.

The term "average" as used herein, refers to a value that is an average of values derived from a variable amount of patients and/or subjects given the same treatment and/or compound.

The term "mean average" as used herein, refers to a value that is the sum of the values from the variable population of patients divided by the number of patients in the population given the same treatment and/or compound.

Method of Use

The goal of pharmacologic therapy for the treatment of atrial fibrillation (AF) depends on whether one is treating acute or paroxysmal AF, to induce rapid cardioversion to a normal sinus rhythm, or whether one seeks to prevent AF recurrence with prolonged administration of the drug. In acute or paroxysmal AF in patients who do not have a history of frequent recurrence and perhaps to some extent in recurrent AF, although recurrent AF is more resistant to acute cardioversion by any means, the goal is to rapidly pharmacologically induce cardioversion of a patient who currently is suffering from an AF episode, typically with the administration of a single drug dose or with administration of a limited number of doses. Alternatively, prevention of recurrent AF episodes may require chronic prophylactic treatment.

In the context of treating acute or paroxysmal AF to induce immediate cardioversion, the efficacy of sulcardine and its pharmaceutically acceptable salts is believed to be a function of peak plasma concentration, requiring the maintenance of a high plasma level for a minimal period, for example, of minutes to less than one hour in duration, to afford time for cardioversion to a normal sinus rhythm; after that time, the patient should remain in normal sinus rhythm without the need for continued therapeutic plasma levels of drug, unless some other precipitating event causes a future recurrence of the arrhythmia. These types of patients who have no or only limited prior history of AF episodes have lower risk of recurrence and are typically more successfully cardioverted regardless of the means of intervention; hence, continued drug therapy following cardioversion is not indicated. For the acute or paroxysmal AF indication, it is unnecessary to maintain steady blood levels of the drug (steady drug concentration area under the plasma-time curve) for prolonged periods of time. The use of the drug in this clinical situation is akin to the use of electrical cardioversion to acutely drive the heart back into a normal sinus rhythm.

The efficacy of sulcardine and its pharmaceutically acceptable salts in the treatment of patients with persistent or frequently recurring AF is thought to be a function of the area under the plasma-time curve, rather than of a peak plasma concentration. These patients, with a significant history of prior AF and frequent recurrence, are at much higher risk of recurrence that the acute cohort described above. The atria appear to remodel following frequent or prolonged (chronic) AF episodes, predisposing the patient to a higher risk of future events.

Prevention of recurrent AF or treatment of cardioverted chronic AF patients requires maintaining drug concentration peak and trough concentrations over the dosing period within a range that minimizes the risk of adverse events, associated with high plasma concentrations, and yet that maintains blood levels above some minimally pharmacologically antiarrhythmic) active concentration. Accordingly, in the treatment of recurrent or chronic cardioverted AF patients, administering active agent over a longer period, e.g., by means of a controlled release formulation or by slow intravenous infusion, has a role to play. In the acute/paroxysmal AF medical setting, the goal is to achieve rather high blood levels for a period of minutes out to an hour or two, allowing the heart sufficient time to respond to drug therapy and slip back into a normal sinus rhythm. Loading the drug by a continuous, short-term infusion over this period, as opposed to administering the drug by a rapid IV push, blunts peak plasma concentrations, minimizing the risk of hypotension which can occur with antiarrhythmic agents that possess activity at Ica calcium ion channel or which possess a vagolytic effect, while allowing for the achievement of high blood levels over a period of time sufficient to result in cardioversion.

Provided herein are compositions and methods for administration of sulcardine, or a pharmaceutically acceptable salt thereof, in a subject which allows for a pharmacokinetic/pharmacodynamics (PK/PD) profile suitable for treating AF, e.g., acute or paroxysmal AF. In one embodiment, without being limited by a particular theory, the PK/PD profile is achieved by one or more of the following factors: IV administration for fast Tmax and high Cmax; rapid redistribution to lower arrythmia risk; pan-electrophysiologic effect on ECG; and opposing QTc/TpTe and JTpc profile presenting lower TdeP risk. In one embodiment, without being limited by a particular theory, it is also surprisingly discovered that sulcardine, or a pharmaceutically acceptable salt thereof, can be administered at certain dosages and in a certain route which are quickly effective when measured using certain pharmacokinetic and pharmacodynamics parameters, but also lose effect quickly. Therefore, sulcardine, or a pharmaceutically acceptable salt thereof, can be more safely and effectively administered to subjects using specific dosages, and a specific route of administration, which will also result in beneficial outcomes.

In one aspect, provided herein is a pharmaceutical composition comprising sulcardine, or a pharmaceutically acceptable salt thereof, wherein the composition produces ECG parameter changes including: increases in heart rate (HR), QRS, PDur, PR, and QTcF; reduction of JTp; and no effect or increase in TpTe.

In some embodiments, the pharmaceutical composition comprising sulcardine, or a pharmaceutically acceptable salt thereof, produces dose proportional ECG parameter changes including: increases in QRS, PDur, PR, QTcF; reduction of JTp; and no effect or increase in TpTe. In some embodiments, the pharmaceutical composition comprising sulcardine or a pharmaceutically acceptable salt thereof, produces dose proportional ECG parameter changes including: increases in QRS, PDur, PR, and TpTe. In some embodiments, the pharmaceutical composition comprising sulcardine or a pharmaceutically acceptable salt thereof, produces dose proportional ECG parameter changes including: reduction of JTp. In some embodiments, the pharmaceutical composition comprising sulcardine or a pharmaceutically acceptable salt thereof, produces dose proportional ECG parameter changes including: reduction of JTp. In some embodiments, the pharmaceutical composition comprising sulcardine, or a pharmaceutically acceptable salt thereof, produces dose proportional ECG parameter changes including: no effect or prolonged TpTe interval. In some embodiments, the pharmaceutical composition comprising sulcardine, or a pharmaceutically acceptable salt thereof, produces dose proportional ECG parameter changes including: no effect or prolonged TpTe interval in combination with a reduction of JTp and prolongation in QTc In some embodiments, the pharmaceutical composition comprising sulcardine, or a pharmaceutically acceptable salt thereof, produces one or more ECG parameter changes comprising increases in QRS, PDur, PR, and QTcF of no more than about 25%. In some embodiments, the ECG parameter changes comprise increases in heart rate, and one or more of QRS, PDur, PR, and QTcF of no more than about 25%. In some embodiments, the sulcardine produced ECG parameter changes multiple ECG parameters. In some embodiments, the pharmaceutical composition comprising sulcardine, or a pharmaceutically acceptable salt thereof, produces ECG parameter changes comprising increases in HR of no more than about 25%. In some embodiments, the pharmaceutical composition comprising sulcardine, or a pharmaceutically acceptable salt thereof, produces one or more ECG parameter changes comprising increases in HR, QRS, PDur, PR, and QTcF of about 0.5% to about 20%. In some embodiments, the ECG parameter changes comprising increases in heart rate, QRS, PDur, PR, and QTcF of about 1.0% to about 15%, about 1.0% to about 10%. In some embodiments, the increases in heart rate, QRS, PDur, PR, and QTcF about 0.5%, 1.0%, 1.5%, 2.0%, 2.5%, 3.0%, 3.5%, 4.0%, 4.5%, 5.0%, 5.5%0, 6.0%, 6.5%, 7.0%, 7.5% 8.0%, 8.5%, 9.0%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, or 24.5%; or any percentage change therein. In some embodiments, the increase is not greater than about 25% or about 30%.

In some embodiments, the pharmaceutical composition is an inhibitor of $Na_L$ (late sodium channel), in addition to being an inhibitor of INa (fast sodium channel) and LCa (L-type calcium channel) in the heart. This leads to a biphasic effect on QTc duration characterized by ECG parameter changes which can mitigate the risk of Torsade de Pointes. These ECG parameter changes comprise: (i) no change or a reduction of JTpc of NMT of about 15-25 msec; and (ii) no effect or an increase in TpTe. In some embodiments, the ECG parameter changes comprise inhibition of early after depolarization (EADs). In some embodiments, the ECG parameter changes comprise an increase in QTc interval at lower concentration doses of sulcardine, or a pharmaceutically acceptable salt thereof, followed by a subsequent attenuation in prolongation or shortening in QTc. This is often a result increased $Na_L$ and LCa channel inhibition.

In some embodiments, the ECG parameter maximal changes occur prior to, or at Tmax. In some embodiments, the pharmaceutical composition has no material effect on heart rate or increases heart rate by no more than about 25%, prior to, or at about Tmax. In some embodiments, the pharmaceutical composition has no material effect on heart rate or increases heart rate by no more than about 25%, prior to, or in proximity to Tmax. In some embodiments, the pharmaceutical composition has no material effect on heart rate or increases or decreases diastolic and/or systolic blood pressure by no more than about 25%, prior to, or at about Tmax.

In some embodiments, the pharmaceutical composition does not induce $2^{nd}$ or $3^{rd}$ degree heart block.

In some embodiments, sulcardine or a pharmaceutically acceptable salt thereof, the administration range is from 20 to 1000 mg. In some embodiments, the range is from 20 to 600 mg. In one embodiment, the range is from 100 to 600 mg. In one embodiment, sulcardine or a pharmaceutically acceptable salt thereof, is administrated at a dosage of about 200 mg, 350 mg, 500 mg, or 600 mg. In some embodiments, sulcardine or a pharmaceutically acceptable salt thereof, is administrated at a dosage of about 200 mg, In some embodiments, sulcardine or a pharmaceutically acceptable salt thereof, is administrated at a dosage of about 350 mg. In some embodiments, sulcardine or a pharmaceutically acceptable salt thereof, is administrated at a dosage of about 500 mg. In some embodiments, sulcardine or a pharmaceutically acceptable salt thereof, is administrated at a dosage of about 600 mg.

Dosages are calculated from the free-base (i.e. without an acid counter ion) form of sulcardine.

In some embodiments, the pharmaceutically acceptable salt in the composition is sulcardine sulfate.

In some embodiments, the pharmaceutical composition provided herein further comprises a pharmaceutically acceptable excipient.

In some embodiments, the pharmaceutical composition produces a mean average plasma profile characterized by a Cmax for sulcardine in a subject, after administering 200 mg of sulcardine, from about 1,000 ng/mL to about 2,000 ng/mL, or any range therein, at about Tmax, and at most 25% of Cmax at about 1.0 hours after administration.

In some embodiments, the pharmaceutical composition produces a mean average plasma profile characterized by a Cmax for sulcardine in a subject, after administering 200 mg of sulcardine, of at least about 1,500 ng/mL at about Tmax, and at most 25% of Cmax at about 1.0 hours after administration. In some embodiments, the plasma profile is characterized by a mean average Cmax of at least about 1,000 ng/mL; 1,100 ng/mL; 1,200 ng/mL; 1,300 ng/mL; or 1,400 mg/mL at about Tmax and at most 25% of Cmax at about 1.0 hours after administration.

In some embodiments, the composition produces a mean average plasma profile characterized by a Cmax for the compound (sulcardine) in a subject, after administering 350 mg of the compound (sulcardine), from about 2,000 ng/mL to about 3,500 ng/mL; or any range therein; at about Tmax, and at most 25% of Cmax at about 1.0 hours after administration.

In some embodiment, the pharmaceutical composition produces a mean average plasma profile characterized by a Cmax for the compound (sulcardine) in a subject, after administering 350 mg of the compound (sulcardine), of at least about 3,000 ng/mL at about Tmax, and at most 25% of Cmax at about 1.0 hours after administration. In some embodiments, the plasma profile is characterized by a mean average Cmax of at least about 2,500 ng/mL; 2,600 ng/mL; 2,600 ng/mL; 2,700 ng/mL; 2,800 ng/mL; or 2,900 mg/mL at about Tmax and at most 25% of Cmax at about 1.0 hours after administration.

In some embodiments, the composition produces an mean average plasma profile characterized by a Cmax for the compound (sulcardine) in a subject, after administering 500 mg of the compound (sulcardine), from about 3,500 ng/mL to about 5,000 ng/mL, or any range therein, at about Tmax, and at most 25% of Cmax at about 1.0 hours after administration.

In some embodiments, the pharmaceutical composition produces a mean average plasma profile characterized by a Cmax for the compound (sulcardine) in a subject, after administering 500 mg of the compound (sulcardine), of at least about 4,000 ng/mL at about Tmax, and at most 25% of Cmax at about 1.0 hours after administration. In some embodiments, the plasma profile is characterized by a mean average Cmax of at least about 3,500 ng/mL; 3,600 ng/mL; 3,700 ng/mL; 3,800 ng/mL; or 3,900 mg/mL at about Tmax and at most 25% of Cmax at about 1.0 hours after administration.

In some embodiments, the pharmaceutical composition produces an average plasma profile characterized by a mean average Cmax for the compound (sulcardine) in a subject, after administering 600 mg of the compound (sulcardine), from about 5,000 ng/mL to about 6,000 ng/mL, or any range therein, at about Tmax, and at most 25% of Cmax at about 1.0 hours after administration.

In some embodiments, the pharmaceutical composition produces an mean average plasma profile characterized by a Cmax for the compound (sulcardine) in a subject, after administering 600 mg of the compound (sulcardine), of at least about 5,500 ng/mL at about Tmax, and at most 25% of Cmax at about 1.0 hours after administration. In some embodiments, the plasma profile is characterized by a mean average Cmax of at least about 5,000 ng/mL; 5,100 ng/mL; 5,200 ng/mL; 5,300 ng/mL; or 5,400 mg/mL at about Tmax and at most 25% of Cmax at about 1.0 hours after administration.

In another aspect, provided herein is a method of administering a pharmaceutical composition comprising sulcardine or a pharmaceutically acceptable salt thereof provided herein to a subject in need thereof, wherein a panoply of ECG parameters are changed in the subject. In one embodiment, QRS, PDur, PR, QTcF and TpTe are increased in the subject, and JTp is reduced in the subject. In some embodiments, QRS, PDur, PR, TpTe, and QTcF are increased, and JTp is reduced. In some embodiments, JTp is not changed.

In another aspect, provided herein is a method of treating atrial fibrillation (AF) or atrial flutter, comprising administering to a human subject in need thereof sulcardine, or a pharmaceutically acceptable salt thereof, resulting in ECG parameters comprising an increase in QRS, PDur, PR, QTcF, or any combination thereof, of no more than about 25%. In some embodiments, the ECG parameters further comprise an increase in heart rate (HR) of no more than about 25%. In some embodiments, the ECG parameters further comprise a decrease of no more than about 25 msec in JTp; and no change or an increase in of no more than about 10 msec in TpTe. In some embodiments, JTp is not changed.

In some embodiments, the increases in HR, QRS, PDur, PR, QTcF, or any combination thereof, is from about 0.5% to about 20%. In some embodiments, the increases is about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, or 24.5%; or any percentage change therein In some embodiments, the reduction in JTPc, is from about 0.5% to about 10%. In some embodiments, the reduction in JTpc is about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10%; or any percentage change therein.

In some embodiments, the reduction in JTPc, is from about 10 msec to about 25 msec. In some embodiments, the reduction in JTpc is about 0.5 msec, 1.0 msec, 1.5 msec, 2.0 msec, 2.5 msec, 3.0 msec, 3.5 msec, 4.0 msec, 4.5 msec, 5.0 msec, 5.5 msec, 6.0 msec, 6.5 msec, 7.0 msec, 7.5 msec, 8.0 msec, 8.5 msec, 9.0 msec, 9.5 msec, or 10 msec; or any percentage change therein. In some embodiments, the change in JTpc of NMT is about 15 msec. In some embodiments, there is no change in JTpc In some embodiments, the increase in TpTc, is from about 0.5% to about 10 msec In some embodiments, the increase in TpTe is about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10%; or any percentage change therein.

In some embodiments, the increase in TpTc, is from about 0.5 msec to about 10 msec In some embodiments, the increase in TpTe is about 0.5 msec, 1.0 msec, 1.5 msec, 2.0 msec, 2.5 msec, 3.0 msec, 3.5 msec, 4.0 msec, 4.5 msec, 5.0 msec, 5.5 msec, 6.0 msec, 6.5 msec, 7.0 msec, 7.5 msec, 8.0 msec, 8.5 msec, 9.0 msec, 9.5 msec, or 10 msec; or any percentage change therein. In some embodiments, there is no change in TpTe.

In some embodiments, the administration result in:
(i) an increase of less than about 25% in QRS, PDur, PR, and QTcF:
(ii) a reduction of less than about 25 msec or no change in JTpc: and/or
(iii) no effect or increase in TpTe.

In some embodiments, the QTcF interval in a human subject is increased by from about no more than 60 msec at the end of the administration. In some embodiments, the QTcF interval in a human subject is increased by from about 10 msec to about 340 msec at the end of the administration. In some embodiments, the QTcF interval in a human subject is increased by from about 30 msec to about 60 msec at the end of the administration. In some embodiments, the QT interval is increased by no more than about 50 msec. In some embodiments, the QTcF interval is increased by no more than about 40 msec. In some embodiments, the QTcF interval is increased by no more than about 30 msec. In some embodiments, the QTcF interval is increased by no more than about 20 msec. In some embodiments, the QTcF interval is increased by no more than about 10 msec.

In some embodiments, the composition produces a change in QTcF interval that does not deviate by more than about 20% after administering of the composition. In some embodiments, the composition produces an increased in QTcF interval from about 5% to about 20% after the administration of the composition.

In some embodiments, sulcardine, or a pharmaceutically acceptable salt thereof, is administered at a dose range of from about 20 to about 1000 mg (free-base equivalent). In one embodiment, sulcardine, or a pharmaceutically acceptable salt thereof, is administered at a dose range of from about 20 to about 600 mg. In one embodiment, sulcardine, or a pharmaceutically acceptable salt thereof, is administered at a dose range of from about 60 to about 600 mg. In some embodiments, sulcardine or a pharmaceutically acceptable salt thereof, is administered at a the dose from about 100 to about 600 mg. In some embodiments, sulcardine or a pharmaceutically acceptable salt thereof, is administered at a the dose from 200 to 500 mg. In some embodiments, sulcardine or a pharmaceutically acceptable salt thereof, is administered at a the dose of about 200 mg, 350 mg, 500 mg, or 600 mg. In some embodiments, sulcardine or a pharmaceutically acceptable salt thereof, is administered at a the dose of about 200 mg. In some embodiments, sulcardine or a pharmaceutically acceptable salt thereof, is administered at a the dose of about 350 mg. In some embodiments, sulcardine or a pharmaceutically acceptable salt thereof, is administered at a the dose of about 500 mg. In some embodiments, sulcardine, or a pharmaceutically acceptable salt thereof, is administered at a dose range of from about 100 mg to about 1,000 mg. In some embodiments, sulcardine, or a pharmaceutically acceptable salt thereof, is administered at a dose range of from about 100 mg to about 200 mg, about 100 mg to about 300 mg, about 100 mg to about 400 mg, about 100 mg to about 500 mg, about 100 mg to about 600 mg, about 100 mg to about 700 mg, about 100 mg to about 800 mg, about 100 mg to about 900 mg, about 100 mg to about 1,000 mg, about 200 mg to about 300 mg, about 200 mg to about 400 mg, about 200 mg to about 500 mg, about 200 mg to about 600 mg, about 200 mg to about 700 mg, about 200 mg to about 800 mg, about 200 mg to about 900 mg, about 200 mg to about 1,000 mg, about 300 mg to about 400 mg, about 300 mg to about 500 mg, about 300 mg to about 600 mg, about 300 mg to about 700 mg, about 300 mg to about 800 mg, about 300 mg to about 900 mg, about 300 mg to about 1,000 mg, about 400 mg to about 500 mg, about 400 mg to about 600 mg, about 400 mg to about 700 mg, about 400 mg to about 800 mg, about 400 mg to about 900 mg, about 400 mg to about 1,000 mg, about 500 mg to about 600 mg, about 500 mg to about 700 mg, about 500 mg to about 800 mg, about 500 mg to about 900 mg, about 500 mg to about 1,000 mg, about 600 mg to about 700 mg, about 600 mg to about 800 mg, about 600 mg to about 900 mg, about 600 mg to about 1,000 mg, about 700 mg to about 800 mg, about 700 mg to about 900 mg, about 700 mg to about 1,000 mg, about 800 mg to about 900 mg, about 800 mg to about 1,000 mg, or about 900 mg to about 1,000 mg.

In some embodiments, sulcardine, or a pharmaceutically acceptable salt thereof, is administered at a dose range of from about 100 mg, about 200 mg, about 300 mg, about 400 mg, about 500 mg, about 600 mg, about 700 mg, about 800 mg, about 900 mg, or about 1,000 mg. In some embodiments, sulcardine, or a pharmaceutically acceptable salt thereof, is administered at a dose range of from at least about 100 mg, about 200 mg, about 300 mg, about 400 mg, about 500 mg, about 600 mg, about 700 mg, about 800 mg, or about 900 mg. In some embodiments, sulcardine, or a pharmaceutically acceptable salt thereof, is administered at a dose range of from at most about 200 mg, about 300 mg, about 400 mg, about 500 mg, about 600 mg, about 700 mg, about 800 mg, about 900 mg, or about 1,000 mg.

In another aspect, provided herein is a method of treating atrial fibrillation (AF), comprising parenteral administering to a human subject in need thereof sulcardine, or a pharmaceutically acceptable salt thereof, at a dose of about 200 mg, 350 mg, 500 mg, or 600 mg. In some embodiments, the sulcardine, or a pharmaceutically acceptable salt or solvate thereof is administered at a dose of about 200 mg. In some embodiments, the sulcardine, or a pharmaceutically acceptable salt or solvate thereof is administered at a dose of about 350 mg. In some embodiments, the sulcardine, or a pharmaceutically acceptable salt or solvate thereof is administered at a dose of about 500 mg. In some embodiments, the sulcardine, or a pharmaceutically acceptable salt or solvate thereof is administered at a dose of about 600 mg.

The administration of sulcardine or a pharmaceutically acceptable salt thereof is characterized by PK/PD parameter changes. Sulcardine produces a plasma profile including a dose proportional Cmax in a relatively short Tmax, about equivalent to the time of the end of intravenous infusion or at 30 mins for other parenteral routes. This is followed by a rapid decrease of the compound from the plasma. In some embodiments, the plasma concentration of the sulcardine is decreased by at least 75% within about 1 hour after administration.

In another embodiment, provided herein is a method of treating atrial fibrillation (AF) or atrial flutter, comprising administering to a human subject in need thereof, sulcardine or a pharmaceutically acceptable salt thereof, wherein an amount of sulcardine is sufficient to achieve a Tmax of plasma concentration of sulcardine at about less than 2.0 hours. In some embodiments, the amount of sulcardine is sufficient to achieve a Tmax of plasma concentration of sulcardine from about 0.5 to about 2.0 hours.

In some embodiments, the ECG changes occur prior to, or at about Tmax. In some embodiments, the ECG changes occur prior to, or in proximity to Tmax.

In some embodiments, provided herein is a method of administering a composition provided herein to a subject in need thereof, whereby the compound (sulcardine) produces an average plasma profile characterized by a mean average Cmax for the compound (sulcardine) in a subject, after administering 200 mg of the compound, from about 1,000 ng/mL to about 2,000 ng/mL at about 0.5 hours after administration, and at most 25% of Cmax at about 1.0 hours after administration.

In some embodiments, provided herein is a method of administering a pharmaceutical composition comprising sulcardine or a pharmaceutically acceptable salt thereof, wherein the composition produces a mean average plasma profile characterized by a Cmax for the compound in a subject, after administering 200 mg of the composition, of at least about 1,500 ng/mL at about 0.5 hours after administration, and at most 25% of Cmax at about 1.0 hours after administration.

In some embodiments, provided herein is a method of administering a composition provided herein to a subject in need thereof, whereby the compound (sulcardine) produces a mean average plasma profile characterized by a Cmax for the compound in a subject, after administering 350 mg of the composition, from about 2,000 ng/mL to about 3,000 ng/mL at about 0.5 hours after administration, and at most 25% of Cmax at about 1.0 hours after administration.

In one embodiment, provided herein is a method of administering a pharmaceutical composition comprising sulcardine or a pharmaceutically acceptable salt thereof, wherein the composition produces a mean average plasma profile characterized by a Cmax for the compound in a subject, after administering 350 mg of the compound (sulcardine), of at least about 3,000 ng/mL at about 0.5 hours after administration, and at most 25% of Cmax at about 1.0 hours after administration.

In some embodiments, provided herein is a method of administering a composition provided herein to a subject in need thereof, whereby the compound (sulcardine) produces a mean average plasma profile characterized by a Cmax for the compound (sulcardine) in a subject, after administering 500 mg of the compound (sulcardine), from about 4,000 ng/mL to about 5,000 ng/mL at about 0.5 hours after administration, and at most 25% of Cmax at about 1.0 hours after administration.

In one embodiment, provided herein is a method of administering a pharmaceutical composition comprising sulcardine or a pharmaceutically acceptable salt thereof, wherein the compound (sulcardine) produces a mean average plasma profile characterized by a Cmax for the compound (sulcardine) in a subject, after administering 500 mg of the compound, of at least about 4,000 ng/mL at about 0.5 hours after administration, and at most 25% of Cmax at about 1.0 hours after administration.

In some embodiments, provided herein is a method of administering a composition provided herein to a subject in need thereof, whereby the compound (sulcardine) produces a mean average plasma profile characterized by a Cmax for the compound (sulcardine) in a subject, after administering 600 mg of the compound, from about 5,000 ng/mL to about 6,000 ng/mL at about 0.5 hours after administration, and at most 25% of Cmax at about 1.0 hours after administration.

In some embodiments, provided herein is a method of administering a pharmaceutical composition comprising sulcardine or a pharmaceutically acceptable salt thereof, wherein the compound (sulcardine) produces a mean average plasma profile characterized by a Cmax for the compound in a subject, after administering 600 mg of the compound (sulcardine), of at least about 5,500 ng/mL at about 0.5 hours after administration, and at most 25% of Cmax at about 1.0 hours after administration.

In some embodiments, provided herein is a method of administering a pharmaceutical composition comprising sulcardine or a pharmaceutically acceptable salt thereof, wherein the compound (sulcardine) produces a mean average plasma profile characterized by an AUC for the compound in a subject, after administering 200 mg of the compound, of at least about 1,200 ng·h/mL at about 0.5 hours after administration.

In some embodiments, provided herein is a method of administering a pharmaceutical composition comprising sulcardine or a pharmaceutically acceptable salt thereof, wherein the compound (sulcardine) produces a mean average plasma profile characterized by an AUC for the compound in a subject, after administering 350 mg of the compound, of at least about 2,800 ng·h/mL at about 0.5 hours after administration.

In some embodiments, provided herein is a method of administering a pharmaceutical composition comprising sulcardine or a pharmaceutically acceptable salt thereof, wherein the compound (sulcardine) produces a mean average plasma profile characterized by an AUC for the compound in a subject, after administering 500 mg of the compound, of at least about 4,000 ng·h/mL at about 0.5 hours after administration.

In some embodiments, provided herein is a method of administering a pharmaceutical composition comprising sulcardine or a pharmaceutically acceptable salt thereof, wherein the compound (sulcardine) produces a mean average plasma profile characterized by an AUC for the compound in a subject, after administering 600 mg of the compound, of at least about 5,200 ng·h/mL at about 0.5 hours after administration.

In some embodiments, Tmax is at about 30 minutes.

In one embodiment, sulcardine, or a pharmaceutically acceptable salt thereof, is administered at a dose of from about 60 mg to about 800 mg. In one embodiment, sulcardine, or a pharmaceutically acceptable salt thereof, is administered at a dose of from about 180 mg to about 800 mg. In one embodiment, sulcardine, or a pharmaceutically acceptable salt thereof, is administered at a dose of from about 360 mg to about 800 mg. In one embodiment, sulcardine, or a pharmaceutically acceptable salt thereof, is administered at a dose of from about 400 mg to about 800 mg. In one embodiment, sulcardine, or a pharmaceutically acceptable salt thereof, is administered at a dose of from about 450 mg to about 750 mg. In one embodiment, sulcardine, or a pharmaceutically acceptable salt thereof, is administered at a dose of from about 500 mg to about 700 mg. In one embodiment, sulcardine, or a pharmaceutically acceptable salt thereof, is administered at a dose of from about 550 mg to about 650 mg. In one embodiment, sulcardine, or a pharmaceutically acceptable salt thereof, is administered at a dose of about 600 mg.

In one embodiment, sulcardine, or a pharmaceutically acceptable salt thereof, is administered at a dose of no less than about 60 mg. In one embodiment, sulcardine, or a pharmaceutically acceptable salt thereof, is administered at a dose of no less than about 180 mg. In one embodiment, sulcardine, or a pharmaceutically acceptable salt thereof, is administered at a dose of no less than about 360 mg. In one embodiment, sulcardine, or a pharmaceutically acceptable salt thereof, is administered at a dose of no less than about 400 mg. In one embodiment, sulcardine, or a pharmaceutically acceptable salt thereof, is administered at a dose of no less than about 450 mg. In one embodiment, sulcardine, or a pharmaceutically acceptable salt thereof, is administered at a dose of no less than about 500 mg. In one embodiment, sulcardine, or a pharmaceutically acceptable salt thereof, is administered at a dose of no less than about 550 mg. In one embodiment, sulcardine, or a pharmaceutically acceptable salt thereof, is administered at a dose of no less than about 600 mg. In one embodiment, sulcardine, or a pharmaceutically acceptable salt thereof, is administered at a dose of no less than about 650 mg. In one embodiment, sulcardine, or a pharmaceutically acceptable salt thereof, is administered at a dose of no less than about 700 mg. In one embodiment, sulcardine, or a pharmaceutically acceptable salt thereof, is administered at a dose of no less than about 750 mg. In one embodiment, sulcardine, or a pharmaceutically acceptable salt thereof, is administered at a dose of no less than about 800 mg.

In one embodiment, sulcardine, or a pharmaceutically acceptable salt thereof, is administered at a dose of about 60 mg. In one embodiment, sulcardine, or a pharmaceutically acceptable salt thereof, is administered at a dose of about 180 mg. In one embodiment, sulcardine, or a pharmaceutically acceptable salt thereof, is administered at a dose of about 360 mg. In one embodiment, sulcardine, or a pharmaceutically acceptable salt thereof, is administered at a dose of about 400 mg. In one embodiment, sulcardine, or a pharmaceutically acceptable salt thereof, is administered at a dose of about 450 mg. In one embodiment, sulcardine, or a pharmaceutically acceptable salt thereof, is administered at a dose of about 500 mg. In one embodiment, sulcardine, or a pharmaceutically acceptable salt thereof, is administered at a dose of about 550 mg. In one embodiment, sulcardine, or a pharmaceutically acceptable salt thereof, is administered at a dose of about 600 mg. In one embodiment, sulcardine, or a pharmaceutically acceptable salt thereof, is administered at a dose of about 650 mg.

In one embodiment, the dosages of sulcardine may also include about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, and dosage in between. The dosages may also include about 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, and dosages in between. The dosages of sulcardine may also include about 850 mg, 900 mg, 950 mg and 1,000 mg if it can be shown that such dosages are both safe and have the intended effect.

In one embodiment, sulcardine, or a pharmaceutically acceptable salt thereof, is administered at a dose of about 200 mg, 350 mg, 500 mg or about 600 mg, and dosages in between. In one embodiment, sulcardine, or a pharmaceutically acceptable salt thereof, is administered at a dose of from about 200 mg. In one embodiment, sulcardine, or a pharmaceutically acceptable salt thereof, is administered at a dose of from about 350 mg. In one embodiment, sulcardine, or a pharmaceutically acceptable salt thereof, is administered at a dose of from about 500 mg. In one embodiment, sulcardine, or a pharmaceutically acceptable salt thereof, is administered at a dose of from about 600 mg.

In some embodiments, sulcardine or a pharmaceutically acceptable salt thereof is administered. In some embodiments, sulcardine sulfate is administered. In some embodiments, sulcardine or a pharmaceutically acceptable salt thereof is administered by parenteral administration. In some embodiments, the parenteral administration is intravenous infusion, or intra muscular or subcutaneous injection. In some embodiments, sulcardine or a pharmaceutically acceptable salt thereof is administered by intravenous infusion. In some embodiments, sulcardine or a pharmaceutically acceptable salt thereof is administered by intramuscular injection. In some embodiments, sulcardine or a pharmaceutically acceptable salt thereof is administered orally.

In some embodiments, sulcardine, or a pharmaceutically acceptable salt thereof, is administered as a solution with a concentration of about 50 mg/mL. In some embodiments, the solution is diluted to about 8 mg/ml or less to deliver about 200-500 mg dose in a volume of 50 ml to a patient.

In some embodiments, sulcardine, or a pharmaceutically acceptable salt thereof, is administered over a period of from about 15 minutes to about 2 hours. In some embodiments, sulcardine, or a pharmaceutically acceptable salt thereof, is administered over a period of from about 30 minutes to about 1 hour. In some embodiments, sulcardine, or a pharmaceutically acceptable salt thereof, is administered over a period of less than about 1 hour. In some embodiments, sulcardine, or a pharmaceutically acceptable salt thereof, is administered over a period of about 30 minutes. In some embodiments, sulcardine, or a pharmaceutically acceptable salt thereof, is administered over a period of about 15 minutes.

In some embodiments, sulcardine or a pharmaceutically acceptable salt thereof, is administered at a rate that produces a normal sinus rhythm without producing an arrhythmia or a clinically significant change in heart rate of blood pressure. In some embodiments, sulcardine or a pharmaceutically acceptable salt thereof, is administered at a rate that does not produce an arrhythmia or a clinically significant change in heart rate of blood pressure. In some embodiment, the method increases or decreases diastolic and/or systolic blood pressure by no more than 25%. In some embodiments, the method does not induce a 2$^{nd}$ or 3$^{rd}$ degree heart block.

In some embodiments, sulcardine or a pharmaceutically acceptable salt thereof, is administered from about after the onset of symptoms. In some embodiments, sulcardine or a pharmaceutically acceptable salt thereof, is administered from about 15 minutes to about 72 hours after the onset of symptoms. In some embodiments, sulcardine or a pharmaceutically acceptable salt thereof, is administered no more than about 72 hours after the onset of symptoms. In some embodiments, sulcardine or a salt thereof is administered without need for anti-coagulation. In some embodiments, sulcardine or a pharmaceutically acceptable salt thereof, is administered after less than 7 days after the onset of symptoms without need for anticoagulation. In some embodiments, sulcardine or a pharmaceutically acceptable salt thereof, is administered after about 72 hours after the onset of symptoms and after anti-coagulation therapy.

In the above embodiments, the described ECG parameter changes may be dependent to the level of average plasma concentration and/or average plasma exposure (AUC) of sulcardine or a pharmaceutically acceptable salt thereof in a given patient. In some embodiments, the level of average plasma concentration and/or average plasma exposure (AUC) of sulcardine or a pharmaceutically acceptable salt thereof in a given patient is about 1,000 ng·h/mL to about 10,000 ng·h/mL. In some embodiments, the level of average plasma concentration and/or average plasma exposure (AUC) of sulcardine or a pharmaceutically acceptable salt thereof in a given patient is about 1,000 ng·h/mL to about 2,000 ng·h/mL, about 1,000 ng·h/mL to about 3,000 ng·h/mL, about 1,000 ng·h/mL to about 4,000 ng·h/mL, about 1,000 ng·h/mL to about 5,000 ng·h/mL, about 1,000 ng·h/mL to about 6,000 ng·h/mL, about 1,000 ng·h/mL to about 7,000 ng·h/mL, about 1,000 ng·h/mL to about 8,000 ng·h/mL, about 1,000 ng·h/mL to about 9,000 ng·h/mL, about 1,000 ng·h/mL to about 10,000 ng·h/mL, about 2,000 ng·h/mL to about 3,000 ng·h/mL, about 2,000 ng·h/mL to about 4,000 ng·h/mL, about 2,000 ng·h/mL to about 5,000 ng·h/mL, about 2,000 ng·h/mL to about 6,000 ng·h/mL, about 2,000 ng·h/mL to about 7,000 ng·h/mL, about 2,000 ng·h/mL to about 8,000 ng·h/mL, about 2,000 ng·h/mL to about 9,000 ng·h/mL, about 2,000 ng·h/mL to about 10,000 ng·h/mL, about 3,000 ng·h/mL to about 4,000 ng·h/mL, about 3,000 ng·h/mL to about 5,000 ng·h/mL, about 3,000 ng·h/mL to about 6,000 ng·h/mL, about 3,000 ng·h/mL to about 7,000 ng·h/mL, about 3,000 ng·h/mL to about 8,000 ng·h/mL, about 3,000 ng·h/mL to about 9,000 ng·h/mL, about 3,000 ng·h/mL to about 10,000 ng·h/mL, about 4,000 ng·h/mL to about 5,000 ng·h/mL, about 4,000 ng·h/mL to about 6,000 ng·h/mL, about 4,000 ng·h/mL to about 7,000 ng·h/mL, about 4,000 ng·h/mL to about 8,000 ng·h/mL, about 4,000 ng·h/mL to about 9,000 ng·h/mL, about 4,000 ng·h/mL to about 10,000 ng·h/mL, about 5,000 ng·h/mL to about 6,000 ng·h/mL, about 5,000 ng·h/mL to about 7,000 ng·h/mL, about 5,000 ng·h/mL to about 8,000 ng·h/mL, about 5,000 ng·h/mL to about 9,000 ng·h/mL, about 5,000 ng·h/mL to about 10,000 ng·h/mL, about 6,000 ng·h/mL to about 7,000 ng·h/mL, about 6,000 ng·h/mL to about 8,000 ng·h/mL, about 6,000 ng·h/mL to about 9,000 ng·h/mL, about 6,000 ng·h/mL to about 10,000 ng·h/mL, about 7,000 ng·h/mL to about 8,000 ng·h/mL, about 7,000 ng·h/mL to about 9,000 ng·h/mL, about 7,000 ng·h/mL to about 10,000 ng·h/mL, about 8,000 ng·h/mL to about 9,000 ng·h/mL, about 8,000 ng·h/mL to about 10,000 ng·h/mL, or about 9,000 ng·h/mL to about 10,000 ng·h/mL. In some embodiments, the level of average plasma concentration and/or average plasma exposure (AUC) of sulcardine or a pharmaceutically acceptable salt thereof in a given patient is about 1,000 ng·h/mL, about 2,000 ng·h/mL, about 3,000 ng·h/mL, about 4,000 ng·h/mL, about 5,000 ng·h/mL, about 6,000 ng·h/mL, about 7,000 ng·h/mL, about 8,000 ng·h/mL, about 9,000 ng·h/mL, or about 10,000 ng·h/mL. In some embodiments, the level of average plasma concentration and/or average plasma exposure (AUC) of sulcardine or a pharmaceutically acceptable salt thereof in a given patient is at least about 1,000 ng·h/mL, about 2,000 ng·h/mL, about 3,000 ng·h/mL, about 4,000 ng·h/mL, about 5,000 ng·h/mL, about 6,000 ng·h/mL, about 7,000 ng·h/mL, about 8,000 ng·h/mL, or about 9,000 ng·h/mL. In some embodiments, the level of average plasma concentration and/or average plasma exposure (AUC) of sulcardine or a pharmaceutically acceptable salt thereof in a given patient is at most about 2,000 ng·h/mL, about 3,000 ng·h/mL, about 4,000 ng·h/mL, about 5,000 ng·h/mL, about 6,000 ng·h/mL, about 7,000 ng·h/mL, about 8,000 ng·h/mL, about 9,000 ng·h/mL, or about 10,000 ng·h/mL.

In some embodiments, the level of average plasma concentration and/or average plasma exposure (AUC) of sulcardine or a pharmaceutically acceptable salt thereof in a given patient is about 1,000 ng·h/mL to about 6,500 ng·h/mL. In some embodiments, the level of average plasma concentration and/or average plasma exposure (AUC) of sulcardine or a pharmaceutically acceptable salt thereof in a given patient is about 1,000 ng·h/mL to about 1,500 ng·h/mL, about 1,000 ng·h/mL to about 2,000 ng·h/mL, about 1,000 ng·h/mL to about 2,500 ng·h/mL, about 1,000 ng·h/mL to about 3,000 ng·h/mL, about 1,000 ng·h/mL to about 3,500 ng·h/mL, about 1,000 ng·h/mL to about 4,000 ng·h/mL, about 1,000 ng·h/mL to about 4,500 ng·h/mL, about 1,000 ng·h/mL to about 5,000 ng·h/mL, about 1,000 ng·h/mL to about 5,500 ng·h/mL, about 1,000 ng·h/mL to about 6,000 ng·h/mL, about 1,000 ng·h/mL to about 6,500 ng·h/mL, about 1,500 ng·h/mL to about 2,000 ng·h/mL, about 1,500 ng·h/mL to about 2,500 ng·h/mL, about 1,500 ng·h/mL to about 3,000 ng·h/mL, about 1,500 ng·h/mL to about 3,500 ng·h/mL, about 1,500 ng·h/mL to about 4,000 ng·h/mL, about 1,500 ng·h/mL to about 4,500 ng·h/mL, about 1,500 ng·h/mL to about 5,000 ng·h/mL, about 1,500 ng·h/mL to about 5,500 ng·h/mL, about 1,500 ng·h/mL to about 6,000 ng·h/mL, about 1,500 ng·h/mL to about 6,500 ng·h/mL, about 2,000 ng·h/mL to about 2,500 ng·h/mL, about 2,000 ng·h/mL to about 3,000 ng·h/mL, about 2,000 ng·h/mL to about 3,500 ng·h/mL, about 2,000 ng·h/mL to about 4,000 ng·h/mL, about 2,000 ng·h/mL to about 4,500 ng·h/mL, about 2,000 ng·h/mL to about 5,000 ng·h/mL, about 2,000 ng·h/mL to about 5,500 ng·h/mL, about 2,000 ng·h/mL to about 6,000 ng·h/mL, about 2,000 ng·h/mL to about 6,500 ng·h/mL, about 2,500 ng·h/mL to about 3,000 ng·h/mL, about 2,500 ng·h/mL to about 3,500 ng·h/mL, about 2,500 ng·h/mL to about 4,000 ng·h/mL, about 2,500 ng·h/mL to about 4,500 ng·h/mL, about 2,500 ng·h/mL to about 5,000 ng·h/mL, about 2,500 ng·h/mL to about 5,500 ng·h/mL, about 2,500 ng·h/mL to about 6,000 ng·h/mL, about 2,500 ng·h/mL to about 6,500 ng·h/mL, about 3,000 ng·h/mL to about 3,500 ng·h/mL, about 3,000 ng·h/mL to about 4,000 ng·h/mL, about 3,000 ng·h/mL to about 4,500 ng·h/mL, about 3,000 ng·h/mL to about 5,000 ng·h/mL, about 3,000 ng·h/mL to about 5,500 ng·h/mL, about 3,000 ng·h/mL to about 6,000 ng·h/mL, about 3,000 ng·h/mL to about 6,500 ng·h/mL, about 3,500 ng·h/mL to about 4,000 ng·h/mL, about 3,500 ng·h/mL to about 4,500 ng·h/mL, about 3,500 ng·h/mL to about 5,000 ng·h/mL, about 3,500 ng·h/mL to about 5,500 ng·h/mL, about 3,500 ng·h/mL to about 6,000 ng·h/mL, about 3,500 ng·h/mL to about 6,500 ng·h/mL, about 4,000 ng·h/mL to about 4,500 ng·h/mL, about 4,000 ng·h/mL to about 5,000 ng·h/mL, about 4,000 ng·h/mL to about 5,500 ng·h/mL, about 4,000 ng·h/mL to about 6,000 ng·h/mL, about 4,000 ng·h/mL to about 6,500 ng·h/mL, about 4,500 ng·h/mL to about 5,000 ng·h/mL, about 4,500 ng·h/mL to about 5,500 ng·h/mL, about 4,500 ng·h/mL to about 6,000 ng·h/mL, about 4,500 ng·h/mL to about 6,500 ng·h/mL, about 5,000 ng·h/mL to about 5,500 ng·h/mL, about 5,000 ng·h/mL to about 6,000 ng·h/mL, about 5,000 ng·h/mL to about 6,500 ng·h/mL, about 5,500 ng·h/mL to about 6,000 ng·h/mL, about 5,500 ng·h/mL to about 6,500 ng·h/mL, or about 6,000 ng·h/mL to about 6,500 ng·h/mL. In some embodiments, the level of average plasma concentration and/or average plasma exposure (AUC) of sulcardine or a pharmaceutically acceptable salt thereof in a given patient is about 1,000 ng·h/mL, about 1,500 ng·h/mL, about 2,000 ng·h/mL, about 2,500 ng·h/mL, about 3,000 ng·h/mL, about 3,500 ng·h/mL, about 4,000 ng·h/mL, about 4,500 ng·h/mL, about 5,000 ng·h/mL, about 5,500 ng·h/mL, about 6,000 ng·h/mL, or about 6,500 ng·h/mL. In some embodiments, the level of average plasma concentration and/or average plasma exposure (AUC) of sulcardine or a pharmaceutically acceptable salt thereof in a given patient is at least about 1,000 ng·h/mL, about 1,500 ng·h/mL, about 2,000 ng·h/mL, about 2,500 ng·h/mL, about 3,000 ng·h/mL, about 3,500 ng·h/mL, about 4,000 ng·h/mL, about 4,500 ng·h/mL, about 5,000 ng·h/mL, about 5,500 ng·h/mL, or about 6,000 ng·h/mL. In some embodiments, the level of average plasma concentration and/or average plasma exposure (AUC) of sulcardine or a pharmaceutically acceptable salt thereof in a given patient is at most about 1,500 ng·h/mL, about 2,000 ng·h/mL, about 2,500 ng·h/mL, about 3,000 ng·h/mL, about 3,500 ng·h/mL, about 4,000 ng·h/mL, about 4,500 ng·h/mL, about 5,000 ng·h/mL, about 5,500 ng·h/mL, about 6,000 ng·h/mL, or about 6,500 ng·h/mL.

In some embodiments, the level of average plasma concentration and/or average plasma exposure (AUC) of sulcardine or a pharmaceutically acceptable salt thereof in a given patient is about 100 ng·h/mL to about 1,000 ng·h/mL. In some embodiments, the level of average plasma concentration and/or average plasma exposure (AUC) of sulcardine or a pharmaceutically acceptable salt thereof in a given patient is about 100 ng·h/mL to about 200 ng·h/mL, about 100 ng·h/mL to about 300 ng·h/mL, about 100 ng·h/mL to about 400 ng·h/mL, about 100 ng·h/mL to about 500 ng·h/mL, about 100 ng·h/mL to about 600 ng·h/mL, about 100 ng·h/mL to about 700 ng·h/mL, about 100 ng·h/mL to about 800 ng·h/mL, about 100 ng·h/mL to about 900 ng·h/mL, about 100 ng·h/mL to about 1,000 ng·h/mL, about 200 ng·h/mL to about 300 ng·h/mL, about 200 ng·h/mL to about 400 ng·h/mL, about 200 ng·h/mL to about 500 ng·h/mL, about 200 ng·h/mL to about 600 ng·h/mL, about 200 ng·h/mL to about 700 ng·h/mL, about 200 ng·h/mL to about 800 ng·h/mL, about 200 ng·h/mL to about 900 ng·h/mL, about 200 ng·h/mL to about 1,000 ng·h/mL, about 300 ng·h/mL to about 400 ng·h/mL, about 300 ng·h/mL to about 500 ng·h/mL, about 300 ng·h/mL to about 600 ng·h/mL, about 300 ng·h/mL to about 700 ng·h/mL, about 300 ng·h/mL to about 800 ng·h/mL, about 300 ng·h/mL to about 900 ng·h/mL, about 300 ng·h/mL to about 1,000 ng·h/mL, about 400 ng·h/mL to about 500 ng·h/mL, about 400 ng·h/mL to about 600 ng·h/mL, about 400 ng·h/mL to about 700 ng·h/mL, about 400 ng·h/mL to about 800 ng·h/mL, about 400 ng·h/mL to about 900 ng·h/mL, about 400 ng·h/mL to about 1,000 ng·h/mL, about 500 ng·h/mL to about 600 ng·h/mL, about 500 ng·h/mL to about 700 ng·h/mL, about 500 ng·h/mL to about 800 ng·h/mL, about 500 ng·h/mL to about 900 ng·h/mL, about 500 ng·h/mL to about 1,000 ng·h/mL, about 600 ng·h/mL to about 700 ng·h/mL, about 600 ng·h/mL to about 800 ng·h/mL, about 600 ng·h/mL to about 900 ng·h/mL, about 600 ng·h/mL to about 1,000 ng·h/mL, about 700 ng·h/mL to about 800 ng·h/mL, about 700 ng·h/mL to about 900 ng·h/mL, about 700 ng·h/mL to about 1,000 ng·h/mL, about 800 ng·h/mL to about 900 ng·h/mL, about 800 ng·h/mL to about 1,000 ng·h/mL, or about 900 ng·h/mL to about 1,000 ng·h/mL. In some embodiments, the level of average plasma concentration and/or average plasma exposure (AUC) of sulcardine or a pharmaceutically acceptable salt thereof in a given patient is about 100 ng·h/mL, about 200 ng·h/mL, about 300 ng·h/mL, about 400 ng·h/mL, about 500 ng·h/mL, about 600 ng·h/mL, about 700 ng·h/mL, about 800 ng·h/mL, about 900 ng·h/mL, or about 1,000 ng·h/mL. In some embodiments, the level of average plasma concentration and/or average plasma exposure (AUC) of sulcardine or a pharmaceutically acceptable salt thereof in a given patient is at least about 100 ng·h/mL, about 200 ng·h/mL, about 300 ng·h/mL, about 400 ng·h/mL, about 500 ng·h/mL, about 600 ng·h/mL, about 700 ng·h/mL, about 800 ng·h/mL, or about 900 ng·h/mL. In some embodiments, the level of average plasma concentration and/or average plasma exposure (AUC) of sulcardine or a pharmaceutically acceptable salt thereof in a given patient is at most about 200 ng·h/mL, about 300 ng·h/mL, about 400 ng·h/mL, about 500 ng·h/mL, about 600 ng·h/mL, about 700 ng·h/mL, about 800 ng·h/mL, about 900 ng·h/mL, or about 1,000 ng·h/mL.

In some embodiments, the level of average plasma concentration and/or average plasma exposure (AUC) of sulcardine or a pharmaceutically acceptable salt thereof in a given patient, as embodied above, is reached prior to, or at, Tmax. In some embodiments, the level of average plasma concentration and/or average plasma exposure (AUC) of sulcardine or a pharmaceutically acceptable salt thereof in a given patient, as embodied above, is achieved at about 5% Tmax to about 95% Tmax. In some embodiments, the level of average plasma concentration and/or average plasma exposure (AUC) of sulcardine or a pharmaceutically acceptable salt thereof in a given patient, as embodied above, is achieved at about 5% Tmax to about 10% Tmax, about 5% Tmax to about 20% Tmax, about 5% Tmax to about 30% Tmax, about 5% Tmax to about 40% Tmax, about 5% Tmax to about 50% Tmax, about 5% Tmax to about 60% Tmax, about 5% Tmax to about 70% Tmax, about 5% Tmax to about 80% Tmax, about 5% Tmax to about 90% Tmax, about 5% Tmax to about 95% Tmax, about 10% Tmax to about 20% Tmax, about 10% Tmax to about 30% Tmax, about 10% Tmax to about 40% Tmax, about 10% Tmax to about 50% Tmax, about 10% Tmax to about 60% Tmax, about 10% Tmax to about 70% Tmax, about 10% Tmax to about 80% Tmax, about 10% Tmax to about 90% Tmax, about 10% Tmax to about 95% Tmax, about 20% Tmax to about 30% Tmax, about 20% Tmax to about 40% Tmax, about 20% Tmax to about 50% Tmax, about 20% Tmax to about 60% Tmax, about 20% Tmax to about 70% Tmax, about 20% Tmax to about 80% Tmax, about 20% Tmax to about 90% Tmax, about 20% Tmax to about 95% Tmax, about 30% Tmax to about 40% Tmax, about 30% Tmax to about 50% Tmax, about 30% Tmax to about 60% Tmax, about 30% Tmax to about 70% Tmax, about 30% Tmax to about 80% Tmax, about 30% Tmax to about 90% Tmax, about 30% Tmax to about 95% Tmax, about 40% Tmax to about 50% Tmax, about 40% Tmax to about 60% Tmax, about 40% Tmax to about 70% Tmax, about 40% Tmax to about 80% Tmax, about 40% Tmax to about 90% Tmax, about 40% Tmax to about 95% Tmax, about 50% Tmax to about 60% Tmax, about 50% Tmax to about 70% Tmax, about 50% Tmax to about 80% Tmax, about 50% Tmax to about 90% Tmax, about 50% Tmax to about 95% Tmax, about 60% Tmax to about 70% Tmax, about 60% Tmax to about 80% Tmax, about 60% Tmax to about 90% Tmax, about 60% Tmax to about 95% Tmax, about 70% Tmax to about 80% Tmax, about 70% Tmax to about 90% Tmax, about 70% Tmax to about 95% Tmax, about 80% Tmax to about 90% Tmax, about 80% Tmax to about 95% Tmax, or about 90% Tmax to about 95% Tmax. In some embodiments, the level of average plasma concentration and/or average plasma exposure (AUC) of sulcardine or a pharmaceutically acceptable salt thereof in a given patient, as embodied above, is achieved at about 5% Tmax, about 10% Tmax, about 20% Tmax, about 30% Tmax, about 40% Tmax, about 50% Tmax, about 60% Tmax, about 70% Tmax, about 80% Tmax, about 90% Tmax, or about 95% Tmax. In some embodiments, the level of average plasma concentration and/or average plasma exposure (AUC) of sulcardine or a pharmaceutically acceptable salt thereof in a given patient, as embodied above, is achieved at about at least about 5% Tmax, about 10% Tmax, about 20% Tmax, about 30% Tmax, about 40% Tmax, about 50% Tmax, about 60% Tmax, about 70% Tmax, about 80% Tmax, or about 90% Tmax. In some embodiments, the level of average plasma concentration and/or average plasma exposure (AUC) of sulcardine or a pharmaceutically acceptable salt thereof in a given patient, as embodied above, is achieved at about at most about 10% Tmax, about 20% Tmax, about 30% Tmax, about 40% Tmax, about 50% Tmax, about 60% Tmax, about 70% Tmax, about 80% Tmax, about 90% Tmax, or about 95% Tmax.

In some embodiments, the AF is acute AF.
In some embodiments, the AF is paroxysmal AF.
In some embodiments, the AF is recurrent AF.
In some embodiments, the treatment is for atrial flutter.

EXAMPLES

Aspects of the present disclosure may be further understood in light of the following examples, which should not be construed as limiting the scope of the present disclosure in any way.

Abbreviation

AE adverse event
AF atrial fibrillation
AF of recent onset an episode of atrial fibrillation, ongoing at the time of dosing with a duration of 2 to 72 hours, as reported by the patient or clinically diagnosed by electrocardiogram (ECG). The episode may be the first known event in a patient with new-onset AF or it may be a recurrent event in patients with paroxysmal AF.
APA amplitude of action potential
APD action potential duration
AUC area under the plasma concentration-time curve
AUC(0-24) area under the plasma concentration-time curve from time 0 to 24 hours after dosing
AUC(0-inf) area under the plasma concentration-time curve from time 0 extrapolated to infinity
AUC(0-last) area under the plasma concentration-time curve from time 0 to the last quantifiable concentration
BP blood pressure
BPM beats per minute
CE concentration effect
CI confidence interval
CL total clearance
CLr renal clearance
Cmax maximum observed plasma concentration
CV % percent coefficient of variation
CYP2D6 cytochrome P450 2D6
ECG electrocardiogram
EF ejection fraction
HF heart failure
IV intravenous
LVEF left ventricular ejection fraction
MI myocardial infarction
MRT mean residence time
msec millisecond
PCI percutaneous coronary intervention
PK pharmacokinetic
PVC premature ventricular contraction
QRS interval from the end of the PR interval to the end of the S wave
QTc corrected QT interval
QTcF QT interval corrected for heart rate using Fridericia's formula
SD standard deviation
SR sinus rhythm
$t_{1/2}$ apparent elimination half-life
TdP Torsades de Pointes
Tmax time to achieve the maximum observed plasma concentration
Vmax maximum depolarization speed Example 1—Administration of Sulcardine HBI-3000 (sulcardine sulfate) was administered to human subjects according to the protocol provided in (Clinical Trials.gov Identifier: NCT03397641. That protocol is incorporated herein by reference in its entirety.

Background: HBI-3000 is a multi-ion channel blocker with relatively balanced in vitro inhibitory effects on $I_{Na-Peak}$, $I_{Na-Late}$, $I_{Ca,L}$ and $I_{Kr}$ developed for the conversion of recent onset atrial fibrillation (AF).

Objective: Provided herein are the safety, tolerability, pharmacokinetics and electrocardiogram (ECG) results of a Phase 1 single ascending dose trial of intravenous (IV) HBI-3000 in healthy subjects. Selected ECG parameters and abbreviations are shown in Table 1.

TABLE 1

ECG parameters and abbreviations.

| Parameter | ECG Variable | Baseline Corrected ECG Variable (ΔECG) | Baseline and Pooled Placebo Corrected ECG Variable (ΔΔECG) |
|---|---|---|---|
| Heart rate, bpm | HR | ΔHR | ΔΔHR |
| PR interval, msec | PR | ΔPR | ΔΔPR |
| P-wave duration, msec | PDur | ΔPDur | ΔΔPDur |
| QRS interval, msec | QRS | ΔQRS | ΔΔQRS |
| Fridericia-corrected QT interval, msec | QTcF | ΔQTcF | ΔΔQTcF |
| J to T peak interval, | JTp | ΔJTp | ΔΔJTp |
| T peak to T end interval, msec | TpTe | ΔTpTe | ΔΔTpTe |

Methods: Forty-seven subjects were randomized to 6 cohorts of 8 subjects to receive 1 of 5 single ascending iv doses (Table 2) of HBI-3000 or placebo (6:2), with 2 cohorts receiving the 600 mg dose. Doses of HBI-3000 ranged from 20 mg (Cohort A), 60 mg (Cohort B), 180 mg (Cohort C), 360 mg (Cohort D), to 600 mg (Cohort E and F). Drug was a lyophilized powder, reconstituted to 50 ml/ml then diluted in saline for delivery via intravenous infusion as a 50 mL solution over 30 minutes.

Continuous 12-lead Holter ECG data were recorded at baseline and 11 time points thereafter. Mean baseline and placebo subtracted (ΔΔ) ECG intervals (QTcF, HR, PR, QRS, and P-wave duration [PDur]) and T-wave segments (J to T peak [JTp] and T peak to T end [TpTe]) were calculated at Cmax for each dose.

Results: HBI-3000 was well tolerated with no dose limiting adverse events or arrhythmias observed.

Table 2 summarizes ECG data at Cmax for each dose, as predicted by mixed-effects modeling. HBI-3000 induced dose-proportional changes in all ECG parameters. The increases in QRS and PDur are consistent with block of $I_{Na-Peak}$. The increase in the PR interval is consistent with the increase in PDur and with both $I_{Na-Peak}$ and $I_{Ca,L}$ inhibition. Prolongation of TpTe is consistent with $I_{Kr}$ block, which would be expected, in isolation, to lengthen JTp as well. The observed dose-related reduction of JTp is likely due to counteraction of the effect of HBI-3000 on $I_{Kr}$ through its inhibition of both $I_{Na-Late}$ and $I_{Ca,L}$.

pharmacodynamically active in human subjects, but also becomes quickly ineffective. In other words, the compound may be administered in certain dosages which results in quick effects in the subject, and then the compound is no longer effective on the cardiovascular system of the subject. It is unknown by what route the compound is removed from or isolated from the cardiovascular system so that it is not effective. However, it has been discovered that when sulcardine sulfate is administered in an amount from about 400 mg to about 800 mg according to the protocol above, the compound is quickly effective and then quickly loses its effect. Those of skill in the art will recognize that these effects may further enhance the safety profile of the compound whereby certain dosages, and/or dosage forms, may be prepared and administered which avoid unwanted side effects.

TABLE 2

| ΔΔECG by Dose from Concentration-Effect Regression Model | | | | | | | |
|---|---|---|---|---|---|---|---|
| Mean, msec or bpm | ΔΔQTcF | ΔΔHR | ΔΔPR | ΔΔQRS | ΔΔPDur | ΔΔJTp | ΔΔTpTe |
| Dose, Cmax (N) | | | | | | | |
| 20 mg, 135 ng/ml (6) | 1.40 | 1.74 | 5.08 | −0.08 | 3.17 | −2.87 | 1.95 |
| 60 mg, 378 ng/ml (6) | 2.35 | 2.21 | 6.06 | 0.54 | 3.71 | −5.28 | 2.20 |
| 180 mg, 1530 ng/ml (6) | 6.89 | 4.44 | 10.73 | 3.50 | 6.24 | −15.09 | 3.37 |
| 360 mg, 3120 ng/ml (5) | 13.50 | 7.70 | 17.53 | 7.81 | 9.93 | −24.60 | 5.07 |
| 600 mg, 5280 ng/ml (12) | 23.77 | 12.75 | 28.10 | 14.50 | 15.67 | −28.10 | 7.72 |
| Slope | 0.0039 | 0.0019 | 0.0040 | 0.0026 | 0.0022 | −0.0000 | 0.0010 |
| P value | <0.0001 | <0.0001 | <0.0001 | <0.0001 | <0.001 | <0.0001 | <0.0001 |

Table 3 shows selected pharmacokinetic data for each dose.

TABLE 3

| Selected pharmacokinetic data. | | | | | | | |
|---|---|---|---|---|---|---|---|
| Dose of HBI-3000 | N | Tmax Mean (h) (Min-Max) | Cmax (ng/mL) (G. CV (%)) | AUC (0-24) (ng h/mL) (G. CV (%)) | AUC (0-last) (ng h/mL) (G. CV (%)) | AUC (0-inf) (ng h/mL) (G. CV (%)) | $T_{1/2}$ (h) (G. CV (%)) |
| 20 mg | 6 | 0.42 (0.25-0.52) | 131 (29.60) | 89.7 (53.00) | 86.2 (54.80) | 175 (NC) | 0.62 (NC) |
| 60 mg | 6 | 0.38 (0.25-0.52) | 369 (23.80) | 299 (17.40) | 306 (18.30) | 312 (NC) | 9.16 (NC) |
| 180 mg | 6 | 0.46 (0.25-0.50) | 1430 (41.60) | 1270 (25.60) | 1550 (23.00) | 2050 (41.80) | 54.76 (32.8) |
| 360 mg | 5 | 0.45 (0.27-0.50) | 3170 (17.60) | 2960 (23.70) | 3470 (26.60) | 3830 (33.80) | 43.68 (48.9) |
| 600 mg | 12 | 0.46 (0.25-0.50) | 5580 (30.50) | 5810 (31.20) | 6640 (30.50) | 7580 (28.90) | 41.14 (20.7) |

In some instances, the patient is administered 350 mg of HBI-3000. Table 4 shows selected pharmacokinetic data for 350 mg dose.

TABLE 4

| Pharmacokinetic data at 350 mg. | | | | | | |
|---|---|---|---|---|---|---|
| Dose of HBI-3000 | Tmax (h) | Cmax (ng/mL) | AUC (0-24) (ng h/mL) | AUC (0-last) (ng h/mL) | AUC (0-inf) (ng h/mL) | $T_{1/2}$ (h) |
| 350 mg | 0.45 | 3080 | 2878 | 3374 | 3723 | 43 |

Additional finding: when sulcardine sulfate is administered at certain dosages, the compound not only becomes Conclusions: These data demonstrate that HBI-3000 is a potent inhibitor of multiple cardiac ion channels that play a role in onset and maintenance of AF. Its strong reduction of JTp may predict freedom from arrhythmias associated with $I_{Kr}$ block. Based on these results and preclinical data indicating low proarrhythmic risk.

Those of skill in the art will also recognize various methods of determining the plasma concentration of sulcardine in a patient at any point in time via enzyme linked assays, including ELISA. Such methods are useful in determining whether the Cmax has been reached in a subject, and when administration of sulcardine may be terminated.

Considering that the expected half-life for oral administration of sulcardine is about 16 hours (See Chen et al., *Fundamental & Clinical Pharmacology*. 31 (2017) 120-125), it was surprising that the present formulation administered as provided herein resulted in the quick "on/off"

profile. Such unexpected results provide an opportunity for more safely providing the intended effects of sulcardine administration as provided in U.S. Pat. Nos. 8,541,464 and 8,637,566. In addition, unlike Chen et al. whereby sulcardine is slowly re-distributed in a subject, it is surprising that the rapid re-distribution of sulcardine in a subject as formulated and administered in the present invention re-distributes quickly. This also provides an avenue for more safely administering sulcardine, and reducing pro-arrhythmic risk.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed:

1. A method of treating atrial fibrillation (AF) or atrial flutter in a patient, comprising administering to the patient a pharmaceutical composition comprising sulcardine or a pharmaceutically acceptable salt thereof, wherein administering the pharmaceutical composition to the patient produces in the patient a change in one or more ECG parameters, wherein the one or more ECG parameters increase by no more than about 25%, further wherein the one or more ECG parameters comprise QRS, PDur, PR, or QTcF, or any combination thereof.

2. The method of claim 1, wherein the ECG parameters further comprise a decrease in JTpc by no more than about 25 msec; and no change in TpTe.

3. The method of claim 1, wherein the ECG parameters further comprise an increases in heart rate (HR) of no more than about 25%; or wherein the ECG parameters further comprise an increase in HR that is not clinically significant.

4. The method of claim 3, wherein the maximum ECG parameter change occurs prior to or at about Tmax.

5. The method of claim 1, wherein the method inhibits early after depolarization.

6. The method of claims 1, wherein the method increases or decreases diastolic and/or systolic blood pressure by no more than about 25%.

7. The method of claims 1, wherein the method does not induce a $2^{nd}$ or $3^{rd}$ degree heart block.

8. The method of claims 1, wherein sulcardine, or a pharmaceutically acceptable salt thereof, is administered at a dose of 200 mg, 350 mg, 500 mg, or 600 mg.

9. The method of claims 1, wherein the pharmaceutically acceptable salt is ethane-1,2-disulfonic acid, naphthalene-1,5-disulfonic acid, 1-hydroxy-2-naphthoic acid, naphthalene-2-sulfonic acid, dihydro sulfonic acid, hydrochloric acid, or hydrobromic acid.

10. The method of claim 1, wherein the QT and/or QRS intervals increases by about 5% to about 20% after the administration of the composition.

11. The method of claim 1, wherein a mean average plasma profile characterized by a Cmax after administering 200 mg of the compound, of at least about 1,500 ng/mL at about Tmax, and at most 25% of Cmax at about 1.0 hours after administration.

12. The method of claims 1, wherein the composition produces a mean average plasma profile characterized by a Cmax after administering 350 mg of the compound, of at least about 3,000 ng/mL at about Tmax, and at most 25% of Cmax at about 1.0 hours after administration.

13. The method claims 1, wherein the composition produces a mean average plasma profile characterized by a Cmax after administering 500 mg of the compound, of at least about 4,000 ng/mL at about Tmax, and at most 25% of Cmax at about 1.0 hours after administration.

14. The method of claims 1, wherein the composition produces a mean plasma profile characterized by an average Cmax after administering 600 mg of the compound, of at least about 5,500 ng/mL at about Tmax, and at most 25% of Cmax at about 1.0 hours after administration.

15. The method of claim 1, wherein administering the pharmaceutical composition to the patient results in a decrease in plasma concentration of at least about 75% within about 1 hour after administration.

16. The method of claims 1, wherein the administration comprises intravenous injection, intramuscular injection, intraperitoneal injections, subcutaneous injection, or oral consumption.

17. The method of claims 1, wherein sulcardine, or a pharmaceutically acceptable salt thereof, is administered over a period less than about 1 hour.

18. The method of claim 17, wherein sulcardine, or a pharmaceutically acceptable salt thereof, is administered over a period of about 30 minutes.

19. The method of claim 17, wherein sulcardine, or a pharmaceutically acceptable salt thereof, is administered over a period of about 15 minutes.

20. The method of claim 1, wherein sulcardine, or a pharmaceutically acceptable salt thereof, is administered at a rate that does not produce an arrhythmia or a clinically significant change in heart rate or blood pressure.

21. The method of claim 1, wherein the AF is acute AF, paroxysmal AF, recurring AF or wherein the treatment is for atrial flutter.

22. The method of claim 1, wherein the method inhibits late sodium channels, fast sodium channels, L-type calcium channels in the heart, or a combination thereof, in the patient.

23. The method of claim 1, wherein a bimodal effect on QTc can occur including prolongation in QTc at lower drug exposure levels (doses) in association with INa cardiac ion channel inhibition followed by a potential plateauing or decrease in QTc interval at higher drug exposure levels (doses) associated with increasing inhibitory effect on NaL and ICa cardiac ion channels.

24. The method of claim 1, wherein the composition results in inhibition of early after depolarizations (EADs).

25. The method of claim 1, wherein an attenuation in prolongation or a shortening in QTc follows an increase in QTc interval.

26. The method of claim 1, wherein the composition is administered to a subject in need by parenteral administration, intravenous infusion or oral consumption.

27. The method of claim 1, wherein the composition produces a mean average plasma profile characterized by a Cmax after administering 350 mg of the compound, of at least about 3,000 ng/mL at about 0.5 hours after administration, and at most 25% of Cmax at about 1.0 hours after administration.

28. The method of claim 1, wherein the composition produces a mean average plasma profile characterized by a Cmax after administering 500 mg of the compound, of at least about 4,000 ng/mL at about 0.5 hours after administration, and at most 25% of Cmax at about 1.0 hours after administration.

29. The method of claim 1, wherein the composition produces a mean average plasma profile characterized by a Cmax after administering 600 mg of the compound, of at least about 5,500 ng/mL at about 0.5 hours after administration, and at most 25% of Cmax at about 1.0 hours after administration.

30. The method of claim 1, wherein the composition produces a mean average plasma profile characterized by an AUC after administering 200 mg of the compound, of at least about 1,200 ng·h/mL at about 0.5 hours after administration.

31. The method of claim 1, wherein the composition produces a mean average plasma profile characterized by an AUC after administering 350 mg of the compound, of at least about 2,800 ng·h/mL at about 0.5 hours after administration.

32. The method of claim 1, wherein the composition produces a mean average plasma profile characterized by an AUC after administering 500 mg of the compound, of at least about 4,000 ng·h/mL at about 0.5 hours after administration.

33. The method of claim 1, wherein the composition produces a mean average plasma profile characterized by an AUC after administering 200 mg of the compound, of at least about 5,200 ng·h/mL at about 0.5 hours after administration.

34. A method of treating atrial fibrillation (AF) or atrial flutter in a human subject, comprising administering to the human subject in need thereof an amount of sulcardine, or a pharmaceutically acceptable salt thereof, wherein amount of sulcardine, or pharmaceutically acceptable salt thereof, is sufficient to achieve a Tmax of plasma concentration of sulcardine, or a pharmaceutically acceptable salt thereof, in the human subject in about less than 2.0 hours.

35. The method of claim 34, wherein the administration results in:
(i) an increase of less than about 25% in QRS, PDur, PR, and QTcF;
(iii) a reduction of less than 10% in JTp; and
(iii) no effect or increase in TpTe.

36. The method of claim 34, wherein the pharmaceutically acceptable salt is ethane-1,2-disulfonic acid, naphthalene-1,5-disulfonic acid, 1-hydroxy-2-naphthoic acid, naphthalene-2-sulfonic acid, hydrochloric acid, or hydrobromic acid.

37. The method of claims 34, wherein the sulcardine, or a pharmaceutically acceptable salt thereof is administered to a subject in need by intravenous injection, intraperitoneal injection, or oral consumption.

38. The method of claim 34, wherein the method produces a change in QTc interval that does not increase by more than about 20% after administration.

39. The method of claims 34, wherein the method produces an increased in QTc interval from about 5% to about 20% after administration.

40. The method of claims 34, wherein the sulcardine, or a pharmaceutically acceptable salt thereof is administered over a period of less than about 1 hour.

41. The method of claim 40, wherein the sulcardine, or a pharmaceutically acceptable salt thereof, is administered over a period of about 30 minutes.

42. The method of claim 40, wherein the sulcardine, or a pharmaceutically acceptable salt thereof, is administered at a rate that does not produce an arrhythmia or a clinically significant change in heart rate of blood pressure.

43. The method of claim 34, wherein the sulcardine, or a pharmaceutically acceptable salt thereof is administered after less than 7 days after the onset of symptoms without need for anticoagulation.

44. The method of claim 34, wherein the sulcardine, or a pharmaceutically acceptable salt thereof is administered no more than 72 hours after the onset of symptoms.

45. The method of claim 34, wherein the AF is acute AF.

* * * * *